(12) United States Patent  (10) Patent No.: US 8,600,000 B2
Fischer  (45) Date of Patent: Dec. 3, 2013

(54) DEVICE AND METHOD FOR A MAMMOGRAPHY APPARATUS

(75) Inventor: Daniel Fischer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 314 days.

(21) Appl. No.: 13/187,712

(22) Filed: Jul. 21, 2011

(65) Prior Publication Data

US 2012/0020455 A1    Jan. 26, 2012

(30) Foreign Application Priority Data

Jul. 21, 2010  (DE) .......................... 10 2010 031 740

(51) Int. Cl.
*A61B 6/04*  (2006.01)
(52) U.S. Cl.
USPC ............................................. 378/37

(58) Field of Classification Search
USPC ......................................... 378/4, 37, 62, 901
See application file for complete search history.

(56) References Cited

U.S. PATENT DOCUMENTS

2006/0140335 A1*  6/2006  Heuscher et al. ................. 378/4
2006/0291611 A1*  12/2006  Pack et al. ......................... 378/4
2008/0212860 A1*  9/2008  Schomberg .................. 382/131

FOREIGN PATENT DOCUMENTS

WO    WO 2008/074681 A1    6/2008

* cited by examiner

*Primary Examiner* — Irakli Kiknadze
(74) *Attorney, Agent, or Firm* — Schiff Hardin LLP

(57) ABSTRACT

The maximum possible vertices for a trajectory are determined with a device for mammography and an associated method, so that the subject to be exposed can be completely imaged on the detector in x-ray acquisitions.

14 Claims, 2 Drawing Sheets

DEVICE AND METHOD FOR A MAMMOGRAPHY APPARATUS

BACKGROUND OF THE INVENTION

1. Field of the Invention

The present invention relates to mammography devices and techniques.

2. Description of the Prior Art

Tomosynthesis represents an extension of classical two-dimensional mammography. For example, a set of 25 x-ray images is created. To obtain these x-ray acquisitions, the x-ray tube is moved on an orbit in a circle segment between +25 and −25 degrees, starting from a perpendicular line set up on the detector surface. X-ray radiation from the x-ray source is then triggered at regular intervals, and the respective x-ray image is read out by the detector and buffered. With a tomosynthesis reconstruction algorithm, a volume set is subsequently created from the multiple projections that are present in digital image data. Depending on the algorithm, a calculation of the digital x-ray image data read out from the detector takes place during or after the conclusion of the x-ray acquisitions. Tissue variations can be localized in the volume set. Tissue variations of different size in a breast are projected differently onto the detector at varying projection angles. During the subsequent reconstruction—for example with the method of filtered back-projection—tissue structures in the breast are enhanced by suitable filtering, displacement and summation. The reconstruction leads to a series of slice images at different depth levels parallel to the detector surface. An analysis of the reconstruction result normally takes place in Z-slices of the volume set that are situated parallel to the detector. The reconstructable tomosynthesis volume is affected by the detector size and deflection of the x-ray head. Given a large deflection of the x-ray head, a better depth resolution can be achieved at the cost of a reduction in size of the reconstructable volume. Given a smaller deflection of the x-ray head, the reconstructable volume increases in size but the depth resolution is correspondingly reduced.

In the creation of a volume set it can occur that the reconstructed volume is smaller than the actual, compressed breast region. This has the disadvantage that no diagnosis can be made with regard to the breast tissue in the border region of the image.

SUMMARY OF THE INVENTION

An object of the invention is to provide an arrangement and an associated method for a mammography apparatus that overcome the aforementioned disadvantage.

The mammography apparatus according to the invention is fashioned such that vertices of the trajectory are established to cause the x-ray exposures of a subject to be respectively completely detected by the detector so that a volume set calculated from the x-ray exposures completely encompasses (represents an image of) the subject. In order to determine the vertices of the trajectory, among other things a 3D model of the subject is created and a straight line is placed between the detector and the x-ray head, with the straight line emanating from the active edge of the detector at a tangent to the surface of the subject. The straight line is a placeholder for an x-ray beam situated on the x-ray cone. The aforementioned x-ray beam is superimposed on the x-ray cone given a perpendicular projection of an extended trajectory curve. For example, a PMD sensor is used to determine the 3D model. Alternatively, a 3D model can be derived from the contact area of the subject on the detector surface during a pre-acquisition.

The invention has the advantage that, given a maximum deflection of the x-ray head depending on the shape of a subject, this can be completely reproduced in the creation of a volume set or of a stereotactic exposure.

The invention also has the advantage that a maximum depth resolution is achieved depending on the acquisition cycle.

The invention has the further advantage that a manual determination of the vertices of the trajectory is omitted.

The invention also has the advantage that the subject area and the subject height are detected, the vertices are determined and the implementation of the tomosynthesis method is thereby optimized in terms of quality and time.

The invention has the advantage that the number of projections and a dose of the projection can be predetermined depending on a determined angle range for a trajectory.

DESCRIPTION OF THE PREFERRED EMBODIMENTS

The maximum possible vertices for a trajectory are determined with this device and the associated method, such that in x-ray acquisitions the subject to be radioscoped can respectively be completely imaged at the detector.

Figure 1:
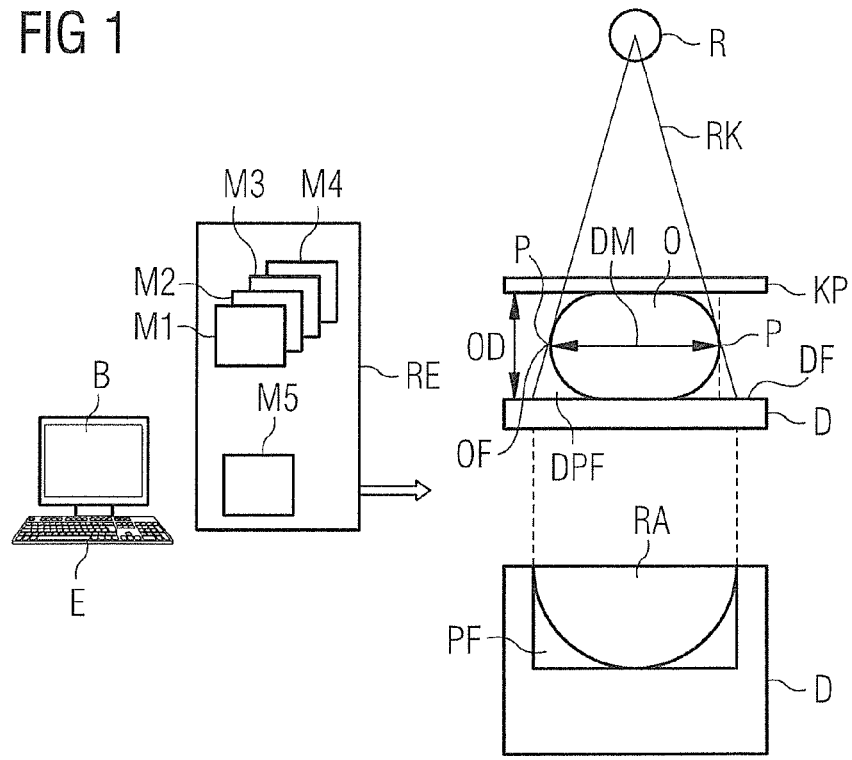
FIG. 1 schematically illustrates the determination of control variables in accordance with the invention.

A front view as well as portions of a plan view on an x-ray device—in particular a mammography system—are schematically shown in FIG. 1. The front view shows an x-ray source R, an acquisition unit shown as a detector and a compression unit with compression plate KP and a detector surface DF opposite this. The x-ray beam emanating from an x-ray source R travels in the shape of a cone RK, for example. For the x-ray acquisitions the subject O arriving for examination is placed and fixed on the surface of the detector DF. To fix a subject O—for example the breast—the compression plate KP is shifted (manually or driven by a motor) in the direction of the detector surface DF, monitored by sensors. A computer RE with an input unit E and monitor unit B is also connected with the x-ray device. In the computer RE the individual modules M1 through M5 are arranged to determine the maximum possible inclination angle of the x-ray head R given simultaneous, integrated detection of a subject O.

The distance between compression plate KP and detector surface DF is determined in a first module M1. If a pre-acquisition already exists for tomosynthesis, the distance of the compression plate KP from the detector surface DF can be detected by means of sensors, for example after termination of the compression of the subject O, possibly while maintaining already detected patient values. The diameter DM of the subject O can be determined via the distance between the points P, for example with an optical or infrared measurement value detection and evaluation in connection with an image detection algorithm or a segmentation algorithm.

In a second module M2 the contact area of the subject O is determined. The contact area of the compressed subject O is detected via sensors in the detector surface or at the underside of the compression plate KP. A middle projection to determine area can likewise be used. The average cross section area DM of the subject can be calculated from the beam sets based on the known geometry of the mammography apparatus and the regularity.

A means to acquire the shape of the surface of a subject is provided in a third module M3. The means is a PMD sensor, for example. The subject O is placed on the contact surface and fixed between contact surface and compression plate. The sensor scans the subject; the measurement data are converted into a 3D model in a computer RE.

In a fourth module M4, the data are retrieved from the preceding modules M1, M2 and M3 and combined into a complete 3D model of the subject O with specification of the position and orientation on the detector surface.

Vertices Rl, Rr of a trajectory T are determined in a fifth module M5, a vertex determination module. For this the constructive vertex data of the mammography apparatus, the data of a possible trajectory and the 3D model created in the fourth module M4 are calculated with position and orientation such that, starting from a deflection of the x-ray head R, a straight line/tangent G, G' between x-ray head R or a collimator output and a boundary region of the detector is drawn as a tangent resting on the 3D model. The straight line/tangent G, G' in this case forms an outermost x-ray beam of an x-ray beam emanating from an x-ray head or, respectively, a controllable collimator.

Figure 2:
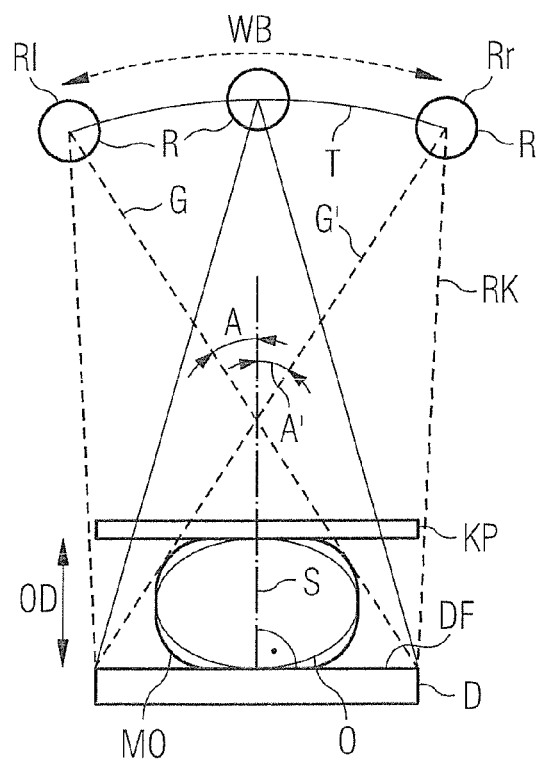
FIG. 2 schematically illustrates the determination of a segment of a trajectory in accordance with the invention.

A schematic illustration to determine a deflection angle of the x-ray head R depending on the shape MO of the subject O is shown in FIG. 2. How the shape MO of the subject O affects the size of the angle range WB of the trajectory T is explained with this schematic illustration. The shape MO is impressed by the breast thickness OD and breast area OF as well as the compression pressure. As already shown and described in connection with FIG. 1, the subject O is arranged on the detector surface DF. The subject O is fixed on the detector surface by means of the compression plate KP during the x-ray acquisitions. A number of x-ray exposures is required in order to create a volume image of the subject O. The digital x-ray data are read out from the detector unit D and calculated by means of recursive calculation algorithms into slice images, for example in the computer RE connected with the mammography unit. During a cycle of multiple x-ray acquisitions the x-ray source R is moved along a predeterminable circle segment WB on a trajectory T. First and second vertex Rl, Rr of the circle segment WB of the trajectory T are shown in FIG. 2. If the right, or second, end point Rr of the trajectory T is considered, this results from the boundary conditions such that the outermost x-rays of the beam cone RK are still received from the boundary region of the subject O, they are also tangent to the boundary region of the subject O. The left or first vertex Rl of the trajectory is determined analogously. Due to the two vertices Rr, Rl of the trajectory T, the angle range WB results in which a sequence of x-ray exposures for tomosynthesis TS can be acquired with a maximum depth resolution. If the patient (or patients) has already had a prior examination, vertex data exist for compression force and the breast thickness and breast area that can be derived from this. Based on the position of the subject O on the detector surface DF, of the 3D model of the subject O, the dimensions of the detector surface DF and the distance of the x-ray tube R from the detector surface DF, a straight line G, G' linking x-ray tube and the boundary region of the detector D can be placed starting from the x-ray tube R, wherein this straight line forms a tangent with the subject.

Figure 3:
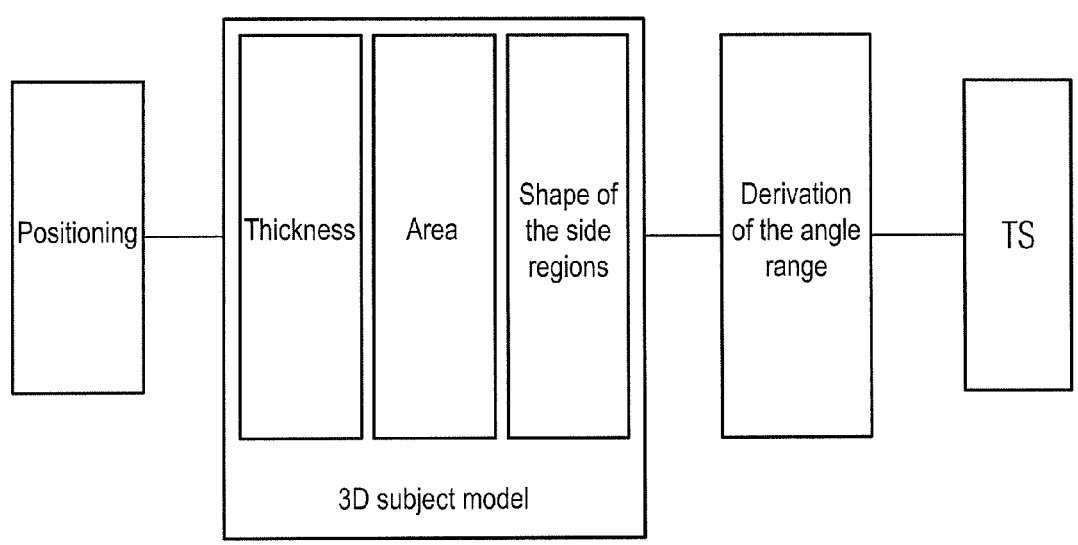
FIG. 3 is a block diagram of an embodiment of the method according to the invention.

A block diagram to determine the optimal tomosynthesis angle WB is shown in FIG. 3. Method steps for the determination of the orientation and fixing of the subject are combined in the first block. Processing units as well as method steps for the creation of an individual 3D breast model are reproduced in the second block. After the subject O has been fixed on the detector surface DF via compression, the distance from the compression plate KP to the detector surface DF is detected by means of sensor units and similarly cached. A 3D model could likewise be determined from pre-exposure and breast thickness. In a subsequent work step, the curvature of the surface of the subject O between compression plate KP and detector surface DF is determined. The curvature of the surface can be detected with a remote image camera based on infrared time of flight measurements. For example, the distance data can be determined with a photon interference detector. The PMD detector is an areal, optical distance sensor capable of spatial resolution, which measures the distance to the subject with the aid of infrared light, for example. For example, the surface curvature of the subject O is detected with the aid of the principle of echo delay travel.

In a module downstream of these three processing procedures, the determined measurement data are combined and a 3D model of the subject O is created.

In the subsequently processing block a tangent G, G' is placed at the surface of the subject that travels in a concave path, wherein the starting point of the tangent G, G' is formed by the still-active edge of the detector D. The enclosed angle A, A' between the tangents G, G' and a perpendicular line S set up virtually on the detector surface DF yields the maximum deflection of the x-ray head R. After the determination of the left-side and right-side vertices Rl, Rr for the deflection of the x-ray head, given a predeterminable number of x-ray acquisitions the distances can be established for the x-ray acquisition in which the x-ray head is halted after the trajectory T is traversed. The radiation exposure for the patient can additionally be varied depending on the number of x-ray acquisitions. In the block TS the calculation procedures of the tomosynthesis reconstruction algorithms are started and the slice images for the volume set are created. The slice images can then be interactively retrieved from caches of the computer RE and output on the monitor B.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device to generate a volume set from x-ray images comprising:
    an x-ray source that is movable along a trajectory relative to a subject to irradiate the subject with x-rays emitted by the x-ray source;
    a radiation detector that detects radiation emitted by the x-ray source and attenuated by the subject, and that generates image data representing x-ray exposures of the subject;
    a vertex determination unit that determines vertices of said trajectory, the vertices of the trajectory being respective locations at which an x-ray beam emitted by said x-ray source forms a tangent to the subject between the x-ray source and the radiation detector; and
    a control unit that controls operation of said x-ray source dependent on the vertices determined by said vertex determination unit.

2. A device as claimed in claim 1 wherein said x-ray source emits said x-rays as an x-ray cone, and wherein said radiation detector is a digital detector, and wherein said vertex determination unit determines said vertices of said trajectory by deflection of said x-ray source that causes an x-ray beam of the x-ray cone to be tangent to the surface of the subject and still detected by said radiation detector.

3. A device as claimed in claim 2 wherein said vertex determination unit determines the respective vertices of said trajectory by using an x-ray beam that is superimposed on said x-ray cone in a projection of a curve of said trajectory.

4. A device as claimed in claim 1 comprising a scanner that scans and evaluates a shape of the subject for use by said control unit.

5. A device as claimed in claim 4 wherein said scanner is a PMD sensor, and produces a 3D scanned model of the subject.

6. A device as claimed in claim 4 wherein said scanner determines the shape of the subject based on 3D models stored in a database, using values scanned from the subject.

7. A device as claimed in claim 6 wherein said 3D model is a deformable 3D model based on values of the subject representing area, compression thickness and compression force.

8. A method to generate a volume set from x-ray images comprising:
   moving an x-ray source along a trajectory relative to a subject and irradiating the subject with x-rays emitted by the x-ray source;
   with a radiation detector, detecting radiation emitted by the x-ray source and attenuated by the subject, and generating image data representing x-ray exposures of the subject;
   in a processor, determining vertices of said trajectory, the vertices of the trajectory being respective locations at which an x-ray beam emitted by said x-ray source forms a tangent to the subject between the x-ray source and the radiation detector; and
   from a control unit, controlling operation of said x-ray source dependent on the determined vertices.

9. A method as claimed in claim 8 comprising emitting said x-rays as an x-ray cone, and determining said vertices of said trajectory by deflection of said x-ray source that causes an x-ray beam of the x-ray cone to be tangent to the surface of the subject and still detected by said radiation detector.

10. A method as claimed in claim 9 comprising determining the respective vertices of said trajectory by using an x-ray beam that is superimposed on said x-ray cone in a projection of a curve of said trajectory.

11. A method as claimed in claim 8 comprising, with a scanner, scanning and evaluating a shape of the subject for use by said control unit.

12. A method as claimed in claim 11 comprising, scanning the subject with a PMD sensor as said scanner, and producing a 3D scanned model of the subject.

13. A method as claimed in claim 11 comprising, with said scanner, determining the shape of the subject based on 3D models stored in a database, using values scanned from the subject.

14. A method as claimed in claim 13 comprising employing, as said 3D model, a deformable 3D model based on values of the subject representing area, compression thickness and compression force.

* * * * *